United States Patent [19]
Weinstein

[11] Patent Number: 5,297,034
[45] Date of Patent: * Mar. 22, 1994

[54] TELEPATHOLOGY DIAGNOSTIC NETWORK

[75] Inventor: Ronald S. Weinstein, Tucson, Ariz.

[73] Assignee: Corabi International Telemetrics, Inc., Alexandria, Va.

[*] Notice: The portion of the term of this patent subsequent to Jun. 1, 2010 has been disclaimed.

[21] Appl. No.: 497

[22] Filed: Jan. 5, 1993

Related U.S. Application Data

[63] Continuation of Ser. No. 462,991, Jan. 5, 1990, Pat. No. 5,216,596, which is a continuation of Ser. No. 44,907, Apr. 30, 1987, abandoned.

[51] Int. Cl.$^5$ .............................................. G06F 15/00
[52] U.S. Cl. .................................... 364/413.02; 382/6
[58] Field of Search ............... 382/6; 358/96; 356/39; 364/413.01, 413.1

[56] References Cited

U.S. PATENT DOCUMENTS

| | | | |
|---|---|---|---|
| 3,805,028 | 4/1974 | Morton | 377/10 |
| 3,833,796 | 9/1974 | Fetner et al. | 364/413.1 |
| 4,054,782 | 10/1977 | Weibel | 364/555 |
| 4,122,518 | 10/1978 | Castleman et al. | 364/413.02 |
| 4,125,828 | 11/1978 | Resnick et al. | 382/6 |
| 4,202,037 | 5/1980 | Glaser et al. | 364/518 |
| 4,203,029 | 5/1980 | Kitchener et al. | 377/10 |
| 4,210,419 | 7/1980 | Castleman | 436/46 |
| 4,320,415 | 3/1982 | Jones | 358/105 |
| 4,523,278 | 6/1985 | Reinhardt et al. | 364/413.1 |
| 4,598,419 | 7/1986 | Mignot et al. | 382/6 |
| 4,656,594 | 4/1987 | Ledley . | |
| 4,709,265 | 11/1987 | Silverman et al. . | |
| 4,724,319 | 9/1988 | Shirota . | |

FOREIGN PATENT DOCUMENTS 0175549 3/1986 European Pat. Off. .
8103223 11/1981 PCT Int'l Appl. .

OTHER PUBLICATIONS

Lee, S. et al. "Computer control of space-born teloperators with sensory feedback", 1985 IEEE Conference on Robotics and Automation St. Louis, Mo., Mar. 1985, 205-214.

Anderson, M. C. et al., "Use of microcomputer to help teach pathology," Journal of Clinical Pathology 1986:39 1140-1142.

Okagaki, T. M.D., and Richart, R. M., "A Closed Circuit Video-Videorecorder Microscope System for Teaching Histopathology", Amer. J. of Clinical Pathology, 1971, vol. 55, No. 1, pp. 73-76.

Forbes, D. J. et al., "Computer-Assisted Mapping With the Light Microscope," *Journal of Neuro-Science Methods*, 1 (1979).

Weinstein, R. S., "Prospects for Telepathology," *Human Pathology*, vol. 17, No. 5 (May 1986) pp. 433-434.

Colburn, D., "The Next Best Thing to Being There," *Washington Post*, Aug. 27, 1986, Health Section, 7.

Sochurek, H. "Medicines New Vision," *National Geographic*, vol. 171, No. 1, Jan. 1987, 2-41.

Primary Examiner—Roy N. Envall, Jr.
Assistant Examiner—Laura Brutman
Attorney, Agent, or Firm—Willian Brinks Hofer Gilson & Lione

[57] ABSTRACT

A system is disclosed for providing pathology diagnostic opinions to physicians at sites remote from where the consulting pathologist is physically located. The system includes a robotically controlled microscope at the remote site equipped with a video camera means for collecting video signals from the microscope. The system also uses a bidirectional communication means to link the microscope with a pathologist workstation. The workstation includes a monitor for viewing images received from the video camera means and control means for generating control signals which are sent over the bidirectional communication means to thereby remotely control the microscope. Preferably, the system also includes means for electronically storing the X, Y, and Z microscope stage coordinates for particular points of the specimen viewed by the pathologist together with means for storing electronically and reproducing photographically the images viewed.

20 Claims, 7 Drawing Sheets

FIG. 8

TELEPATHOLOGY DIAGNOSTIC NETWORK

CROSS-REFERENCE TO RELATED APPLICATION

The present application is a continuation application of U.S. patent application Ser. No. 462,991 filed Jan. 5, 1990 which issued as U.S. Pat. No. 5,216,596 on Jun. 1, 1993 which application was in turn a continuation of U.S. patent application Ser. No. 44,907 filed Apr. 30, 1987, now abandoned.

BACKGROUND OF THE INVENTION

The present invention relates generally to the field of medicine and particularly to the field of of pathology. Pathologists are the physicians responsible for analyzing tissue and liquid specimens by light microscopy. For example, tissue specimens removed at surgery are examined under the microscope by the pathologist who thereafter renders an opinion of the diagnosis. The patients' physician thereafter makes therapeutic decisions based upon the pathologists' diagnosis.

Under current practice, specimens removed from a patient must be delivered to the pathologist who is to examine them. Under the best of circumstances, the examining pathologist works in a laboratory located at the hospital where the patient is. In such a case, the turnaround time can be short enough to allow the pathology diagnostic opinion to be rendered and the opinion to be acted upon during the same operation in which the specimen is removed from the patient. Naturally, being able to make and act on the pathology diagnostic opinion during a single operation is highly desirable.

Alternatively, when the pathologist is not located at the same hospital, the specimens can be sent through the mails or other means to a pathologist working at a diagnostic center at a distant location. This situation precludes removing the specimen and acting on the pathology diagnostic opinion during a single surgical procedure. This result not only adds to the cost of the treatment, but can also lead to adverse health effects inherent in delaying the therapeutic treatment and by subjecting the patient to multiple surgical procedures.

A significant trend in the field of medicine generally and the field of pathology specifically is that of subspecialization. That is, it is more and more common for individual pathologists to develop high levels of expertise in diagnosing the diseases occurring in a single organ system, such as liver or lung. Unfortunately however, most hospitals do not have a sufficient number of patients with diseases in specific organs to justify retaining subspecialty pathologists on a full-time basis. Thus, to obtain opinions from subspecialty pathologists it is required to send the specimens to the facility at which they are located.

A similar problem has been faced in the field of radiology, that is inefficiencies and health-threatening delays resulting from a maldistribution of radiologists and radiology subspecialists. The advent of teleradiology has, to some extent, provided a solution to this problem. Teleradiology is the term used to refer to the practice of establishing networks for telecommunicating the roentgenogram images from the site at which they are produced to the site of a consulting radiologist. Naturally, such a system can be used to eliminate critical delays in providing radiology diagnostic opinions.

Unfortunately, such networking has not been hitherto available in the field of pathology due to critical differences between the way radiology and pathology are practiced. The most prominent difference is the fact that radiologists deal primarily with static black and white images, i.e. roentgenograms which represent large areas of the body. The information content of a single image is thus relatively low. Accordingly, the entire image can be digitized and telecommunicated at an acceptable speed with existing technology.

In contrast, pathologists work with three dimensional samples which need to be viewed in full color by panoramic scanning. In making a diagnosis, the pathologist must be able to view different parts of the sample at different magnifications, at different intensities of illumination, and in full color. The pathologist must also be able to focus up and down through the specimen to view it at different depths. As a result, a network which simply digitizes and transmits static images would not allow a pathologist to render diagnostic opinions in an optimal fashion.

SUMMARY OF THE INVENTION

The present invention is directed to a system which allows a pathologist located at a diagnostic center to render a pathology diagnostic opinion in connection with specimens located at a remote site. Briefly stated, the system comprises a microscope located at the remote site which includes means for robotically adjusting the relative position of a specimen to the objective lens, the magnification of the specimen, and the focus of the microscope. A video camera means is provided for collecting video signals from the microscope. The system also includes a bidirectional communications link between the diagnostic center and the remote site. A pathologist workstation is located at the diagnostic center which includes a monitor for viewing video signals from the video camera means which signals have been sent over the bidirectional communication means. The workstation also includes microscope control means for generating control signals which are sent over the bidirectional communication means to thereby remotely control the microscope.

In accordance with a preferred embodiment, the system also includes means associated with the microscope for generating location signals whereby the X, Y, and Z coordinates of points being viewed are sent over the bidirectional communication means to the pathologist workstation. In addition, the preferred embodiment includes a first microprocessor at the pathologist workstation for processing the control signals to be sent over the bidirectional communication means and for processing the location signals received together with a second microprocessor at the remote site for processing the location signals to be sent over the bidirectional communication means and the control signals received. This preferred system also includes means for generating and graphically displaying a map on a second monitor which map is a representation of the shape of the specimens and also for displaying the relative position on the map of the microscopic field currently being viewed.

In accordance with the most preferred embodiment of the invention, the system includes a plurality of remote sites (e.g. hospitals or clinics without the services of a pathologist or subspecialist). In this way, the network can be used to supply pathology diagnostic services to several remote facilities, thus greatly increasing the efficiencies of the system. Likewise, the most preferred system includes a plurality of diagnostic centers, each with a pathologist workstation linked into the diagnostic network. As a result, the service of pathology subspecialists located around the world can be pooled, both for initial diagnoses and for further consultation.

An important feature of the system of the present invention is that the pathologist at the workstation can not only view the specimen remotely, but he can also control all the functions of the microscope, i.e. stage control, focus, magnification, and illumination. Thus, with the system of the present invention, the pathologist has all the observational faculties available to him through microscopy at his command that he would have if the specimen were present when rendering his diagnostic opinion.

The networking of pathology diagnostic services which the system of the present invention makes possible provides important advantages to the healthcare field. First, it makes it possible for smaller hospitals, clinics, and physicians offices which do not have a pathologist on staff to obtain a pathology diagnostic opinion during a single operation or other tissue sampling procedures such as fine needle aspiration cytology biopsies. It also allows hospitals which do have pathologists, but do not have the pathology subspecialists needed for consultation in a particular situation, to likewise obtain an expert opinion just as quickly as if the pathology subspecialist were present at the hospital.

Another advantage provided by the present invention is the fact that thru the inclusion of more than one diagnostic center in the network, the pathologist who initially views the specimen can obtain a second opinion from other pathologists that are located at different centers. Importantly, this second opinion can be obtained without the delay of sending the sample to the additional consulting pathologist.

Still another advantage of the present invention is that it can be used to further the purposes of medical education. In particular, teaching facilities can be linked to the pathology diagnostic network to thereby give interns and residents a broader range of diagnostic experience, both by observing pathologists work at other diagnostic centers, and by participating in rendering diagnostic opinions themselves. In addition, previous cases which have been electronically archived by the present system can be recalled for educational purposes and to review previous diagnostic practices and diagnostic criteria.

BRIEF DESCRIPTION OF THE DRAWINGS

The present invention will be better understood by way of example and description when read in connection with the following Figures, wherein.

DETAILED DESCRIPTION OF THE PREFERRED EMBODIMENTS

Figure 1:
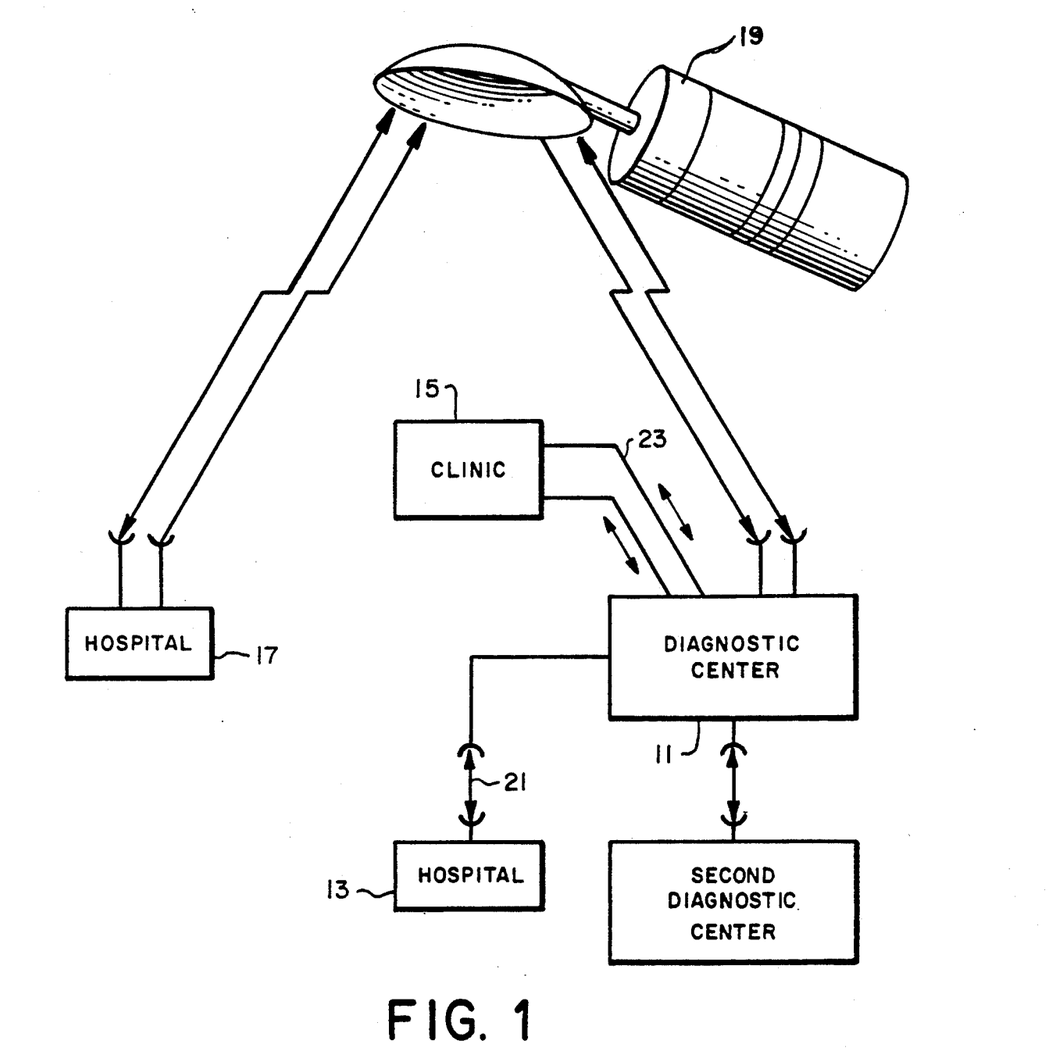
FIG. 1 is a schematic representation of a diagnostic center linked by various bidirectional communication means to remote hospitals, a clinic, and a second diagnostic center.

Referring to the drawings, FIG. 1 depicts a telepathology network according to the present invention. The network includes a diagnostic center 11. Preferably, such an institute will be located at a major tertiary care hospital which is staffed with a panel of pathology subspecialists. Alternatively, the diagnostic center may be a smaller facility which is set up with a single pathologist to render opinions. Accordingly, the term "diagnostic center" as used in this specification and the appended claims should be given a rather broad definition, i.e. a facility at which at least one pathologist can be located to render diagnostic opinions in connection with specimens at remote sites, via the system of the present invention.

As will be explained in more detail below, the most preferred embodiment of the system includes more than one diagnostic center in the network. In particular, it is most preferable to include as many diagnostic centers as possible in the network for at least two reasons. First, it is desirable to provide as many options as possible on where and by whom the specimen is viewed. Second, it is desirable for the pathologist who initially views the specimen to be able to obtain a second opinion almost immediately in difficult or unusual cases.

It is also preferable to include medical teaching facilities as members of the telepathology network. In this way, physicians in training can be educated both as passive observers as they watch expert pathologists at different locations render diagnoses and as actual participants in the diagnosis process.

The network of the present invention also includes remote sites as depicted by hospitals 13 and 17 and clinic 15. Typically, the hospitals and clinics in the network will be those which are too small to retain the services of a full time pathologist. Also, hospitals which have pathologists but do not have the pathology subspecialists that may be needed for a particular diagnosis will also be included in the network. In addition, even large hospitals which employ several subspecialists may want to be included in the network for the purpose of obtaining second opinions from pathologists with similar subspeciality interests at other diagnostic centers. In such a case, it would be desirable to have both a robotically controlled microscope and a pathologist workstation at the same site. In fact, once a pathologist has access to the workstation of the most preferred embodiment, it is likely that he will prefer to have the workstation linked to a microscope at the same site. This will provide the expert pathologist with the capability of performing the specimen mapping functions, described in detail below, will give the pathologist recall, archiving, and reproduction powers not otherwise available.

FIG. 1 is also intended to schematically illustrate different bidirectional telecommunication means by which the remote sites can be linked to the diagnostic center 11. In general, bidirectional communication on means will include broad band transmission for sending the video signal from the remote site to the diagnostic center. The communication means will also require two-way transmission for exchanging data between the two sites. Preferably, the communication means will also provide for two way audio transmission.

As shown, the clinic 15 which is relatively close to the diagnostic center 11 is linked via a coaxial cable 23. Hospital 13 which is located at a greater distance, but not more than about 10 miles, is linked to the diagnostic center 11 via point to point microwave transmission 21. Hospitals located great distances from the diagnostic center 11, such as that shown at 17, can be linked via satellite 19. Indeed, hospitals and diagnostic centers around the world can be linked in a single network via satellites. As a suitable example, a COMSAT-SBS satellite with 32 MHz transponders can be used to relay the necessary signals in both directions.

The details needed to set up the particular bidirectional communications links are known in the art. Suffice it to say that it is required that the bidirectional communications links used in the present invention must be capable of transmitting full color video signals from the video camera to the workstation together with the control signals sent to robotically control the microscope. In addition, the preferred embodiment will also require that location signals, i.e. feedback on the X, Y, and Z coordinates of the specimen being viewed, be sent to the workstation as well.

Figure 2:
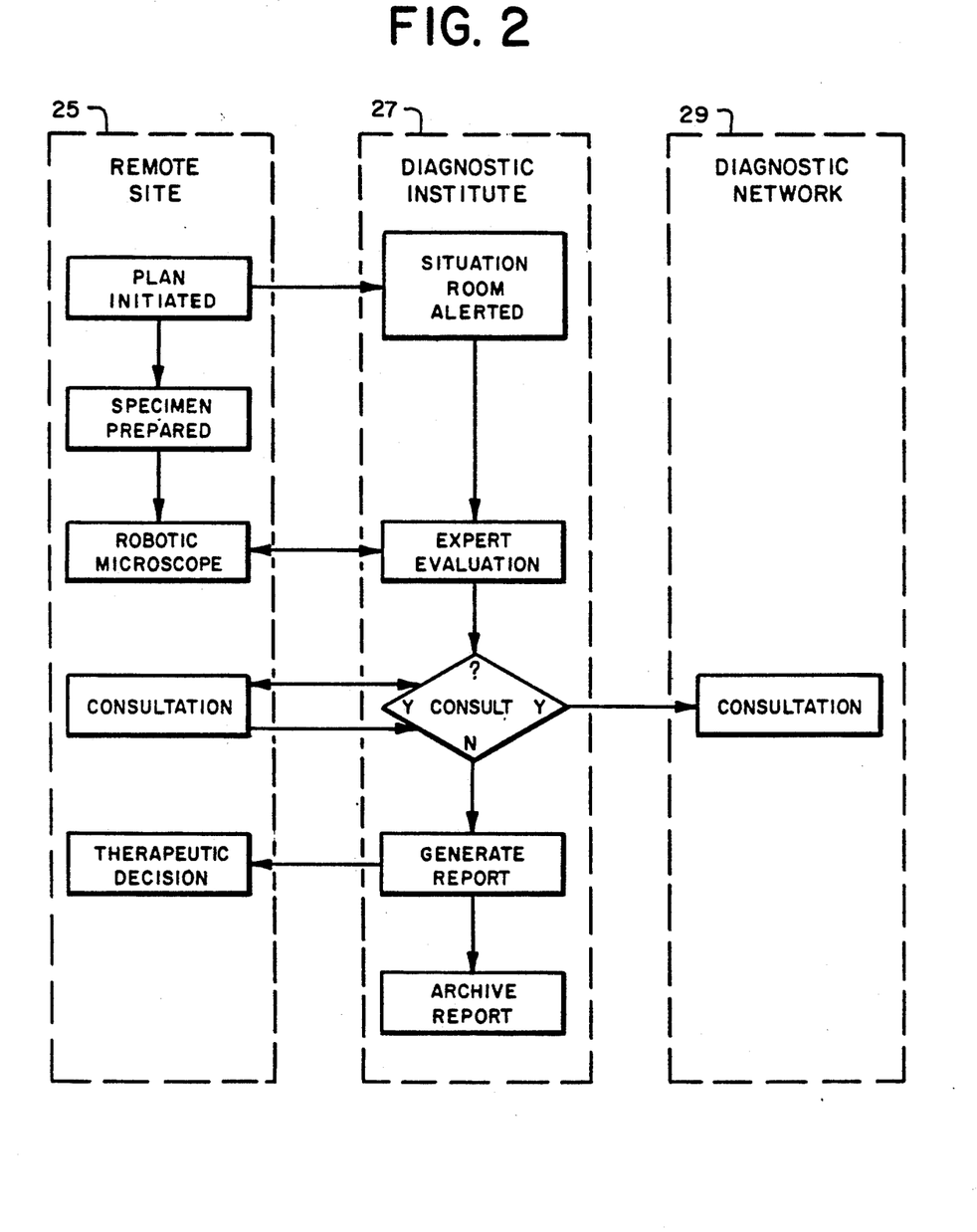
FIG. 2 is a block diagram illustrating a preferred method of using the system of the present invention.

FIG. 2 illustrates a preferred method by which the system of the present invention is employed. The dashed rectangles are intended to show the different sites at which the enclosed steps are performed. The rectangle 25 encloses the steps which are performed at the remote site. Rectangle 27 enclosed the steps which are perfofmed at the diagnostic center. Rectangle 29 encloses the step which may or may not be performed at a second diagnostic center within the diagnostic network.

The first step is the initiation of the plan. In this step, the attending physician at the remote site decides to obtain a specimen and have that specimen analyzed through the diagnostic network.

At this point, the diagnostic center is alerted and inquiry is made as to the availability of a particular pathologist. As stated above, it is preferable that the attending physician at the remote site have the choice of multiple diagnostic centers. In this way, the attending physician is given a broad choice of subspecialists to render the requested opinion. Also, the attending physician has other options available if the pathologist selected is unavailable during the requested time.

It should be noted that although the workstation is intended primarily for use by a physician who has specialized in pathology, it may also be used by other health care professionals such as cytotechnologists or other medical technologists. Thus, as used in this specification and the appended claims, the term "pathologist" is intended to include these other health care professionals as well.

Once the attending physician has arranged for the diagnostic center's participation, the specimen is obtained and prepared. In many cases, the tissue will be obtained from the patient surgically. Alternatively, it may be obtained from bodily fluids or cytology preparations. Accordingly, as used in this specification and the appended claims, the term "specimen" is intended to have a relatively broad definition which includes samples obtained from either a human patient or an animal patient as in veterinary pathology.

Typically, after the tissue is obtained, a frozen section of the specimen is placed on a glass slide, stained and secured in the specimen stage of the robotically controlled microscope equipped with a video camera (see FIG. 5 below) Often, several pieces of tissue are placed on a single slide.

At this point, control of the microscope and video camera functions are taken over by the pathologist at the diagnostic center. In particular, the pathologist will have control over the movement of the stage as well as the magnification, focus and illumination of the microscope. In this way, the pathologist has a level of control in viewing the specimen microscopically comparable to that which he would have if he had the specimen in his possession.

As described in more detail below, the pathologist views the specimen on a video monitor. Importantly, the images seen by the pathologist are in full color, and seen in real time. After viewing the specimen, the pathologist can decide whether or not to consult with the attending physician before making his final report. Preferably, this consultation is facilitated by including means for two-way audio communication as part of the network.

The pathologist can also decide whether to seek consultation with a second pathologist. Naturally this can easily be accomplished when the second pathologist is located at the same diagnostic center. In addition, pathologists located at different diagnostic centers can be included in consultation by providing a workstation at the second institute so that the second pathologist can manipulate and view the specimen on his own and thus render a second opinion with the same speed as if he were present at the first institute.

After consultation, if any, the pathologist makes a report of his diagnostic opinion. This report is communicated to the attending physician, either orally over the audio communication means, in writing by electronic mail, or preferably both. The report is also archived at the diagnostic center for future reference.

Figure 3:
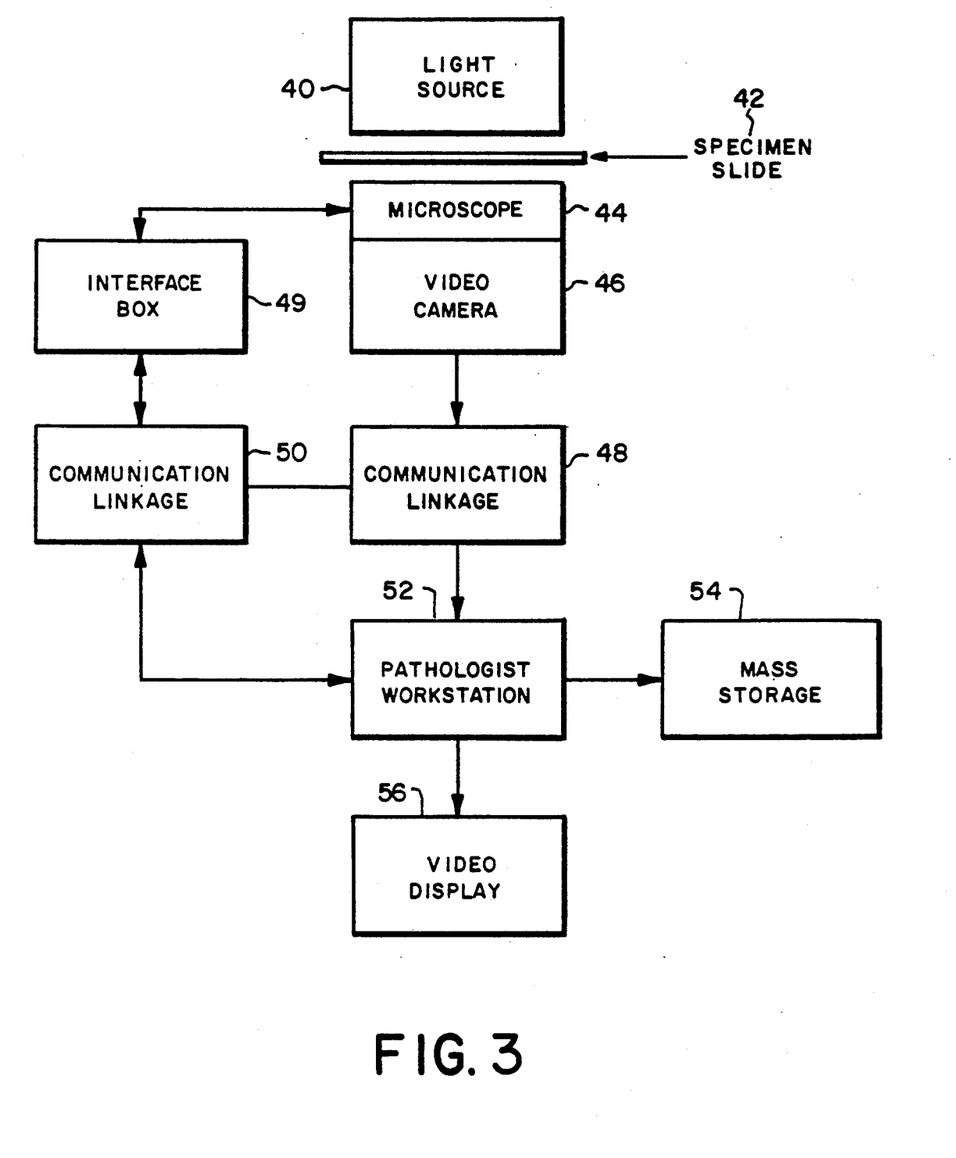
FIG. 3 is a schematic representation of the system of a preferred embodiment the present invention.

FIG. 3 schematically illustrates the primary systems functions of a preferred system of the invention. The specimen is mounted on the slide 42 which is secured to the stage of the microscope 44. The light source 40 of the microscope 44 illuminates the specimen on the slide 42. The image of the specimen is magnified by the lenses of the microscope 44 and picked up and converted to an electronic video signal by the video camera 46. This video signal is transmitted over the communication linkage 48 to the pathologist workstation 52 and viewed by the pathologist on the video display monitor 56. Control signals are generated at the workstation 52 for remotely controlling the functions of the microscope, including stage movement, magnification, focus, and illumination control. These control signals are preferably processed by an inline microprocessor and sent over a communications linkage 50 to the remote site. As a suitable example, an IBM XT can be used as the microprocessor at the remote site. Preferably, the microprocessor is equipped with a modem for transmitting data to and from the telecommunications uplink.

The control signals preferably pass through an interface box at the remote site which converts them to the proper signals to which the computerized microscope will respond. The interface box also preferably converts location signals generated by the microscope to signals which can be used by the microprocessor to determine the X and Y, and preferably Z coordinates of the point of the specimen which is currently being viewed. The Z coordinate reflects the relative vertical distance between the objective lens and the specimen, which vertical distance is adjusted by the focus controls of the microscope.

Figure 4:
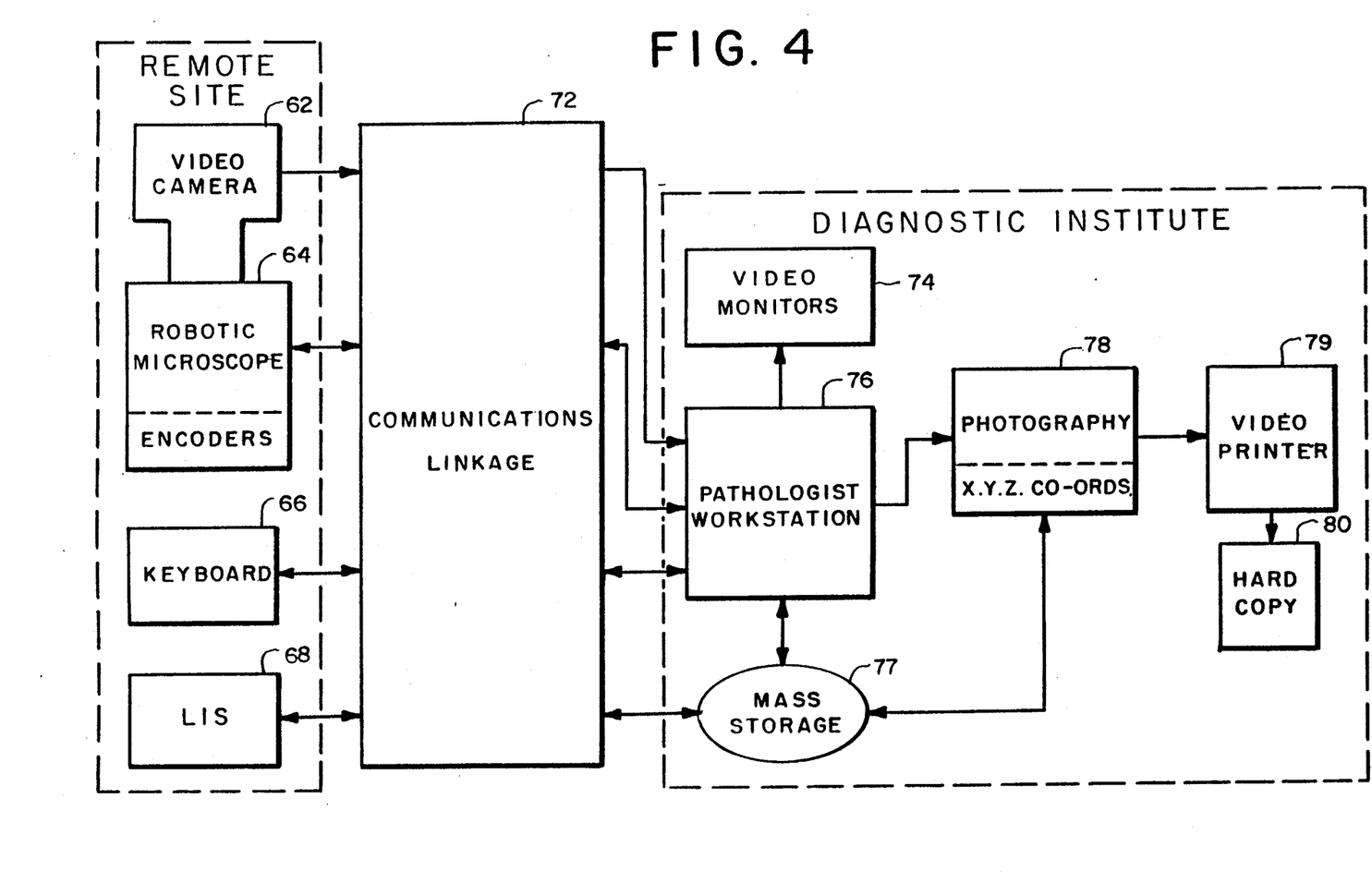
FIG. 4 is a schematic representation of the system of an other preferred embodiment which includes electronic image archiving and electronic photography reproduction capabilities.

FIG. 4 shows schematically the system of an other preferred embodiment. The embodiment depicted here includes an electronic image archiving and photographic reproduction capability. As in the embodiment shown in FIG. 3, the video camera 62 converts the image produced by the robotically controlled microscope 64 into a video signal which is sent over the communications linkage 72 to the pathologist workstation 76 where it is viewed on the video monitor 74. Control signals are generated at the workstation 76 and relayed over the communication linkage 72 to robotically control the functions of the microscope.

In addition, a keyboard 66 is located at the remote site for sending information about the specimen to the workstation 76. Also, the workstation includes the capability to electronically store the information about the sample and the pathologist's report, including the X, Y, and Z coordinates of the particular microscopic field from the specimen which are of interest in the (pathologist's report, in mass storage 77 at the diagnostic center (e.g. on the institute's mainframe computer).

This embodiment further includes means 78 for selecting individual video images, i.e. single video frames, of interest from the specimen. These video images can be stored in mass storage 77 or on floppy disks along with the X, Y, and Z coordinates and other identifying information.

In addition, this embodiment is equipped with a video printer 79 which can provide a hard copy 80, i.e. a full color photographic print, of the images selected. For example, a Hitachi VY-100A video printer may be used.

This embodiment also includes means for sending the pertinent information from the pathologist's report back to the laboratory information system 68, such as the Cerner LIS, in use at the remote site.

Figure 5:
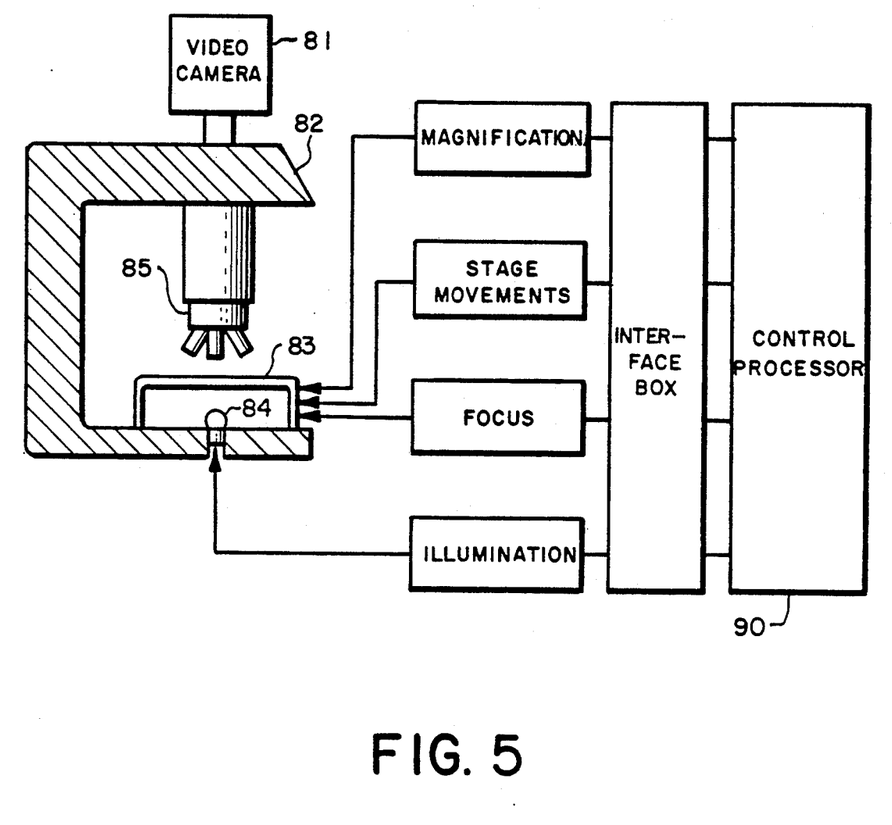
FIG. 5 is a schematic representation of a robotically controlled microscope according to a preferred embodiment of the present invention.

FIG. 5 is a schematic representation of a robotically controlled microscope and its functions according to a preferred embodiment of the present invention. The microscope 82 used in the preferred embodiment is preferably a computer controlled, motorized light microscope, such as an Olympus Vanox equipped with a motorized specimen stage 83, such as one sold by OPELCO, for changing the relative position of the specimen to the objective lens of the microscope.

Magnification of the specimen is adjusted by rotating the motorized nosepiece 85 to thereby select the desired objective lens. Illumination of the specimen is adjusted by controlling the power to the bulb 87 or other light source. Preferably, each of the signals received from the workstation are processed by the microprocessor 90. The motorized stage preferably includes encoders which generate location signals whereby the X and Y coordinates of the point on the specimen currently being viewed can be ascertained at the workstation.

As a suitable example, an IBM XT can be used as the processor at the remote site that is equipped with 640 kilobytes of random access memory, a 10 megabyte hard disk an enhanced graphic card and monitor, a GPIB card, a stage controller card, 2 serial ports, and 1 parallel port. This computer can be programmed according to the source code listing attached hereto as Appendix A.

As mentioned above, an interface box is typically needed in order to convert the control signals received from the workstations into the appropriate signals to which the dedicated processor of the microscope can respond. As an example, an Olympus GPIB interface box can be used with the Olympus Vanox microscope referred to above.

A video camera 81 is attached to the microscope 82 for picking up the magnified image of the specimen and converting it to an electronic video signal. As a suitable example, an Ikegami Model 370-m video camera can be used. The output of the video camera 81 is sent by broad band transmission over the communication means to the workstation. Although not shown, it is also desirable to include a monitor at the remote site so that the attending physician or technician can verify that the images are being captured by the camera. In addition, it may be desirable for the pathologist at the diagnostic institute to show particular microscopic fields to the attending physician at the remote site as he reports his diagnostic opinion.

Figure 6:
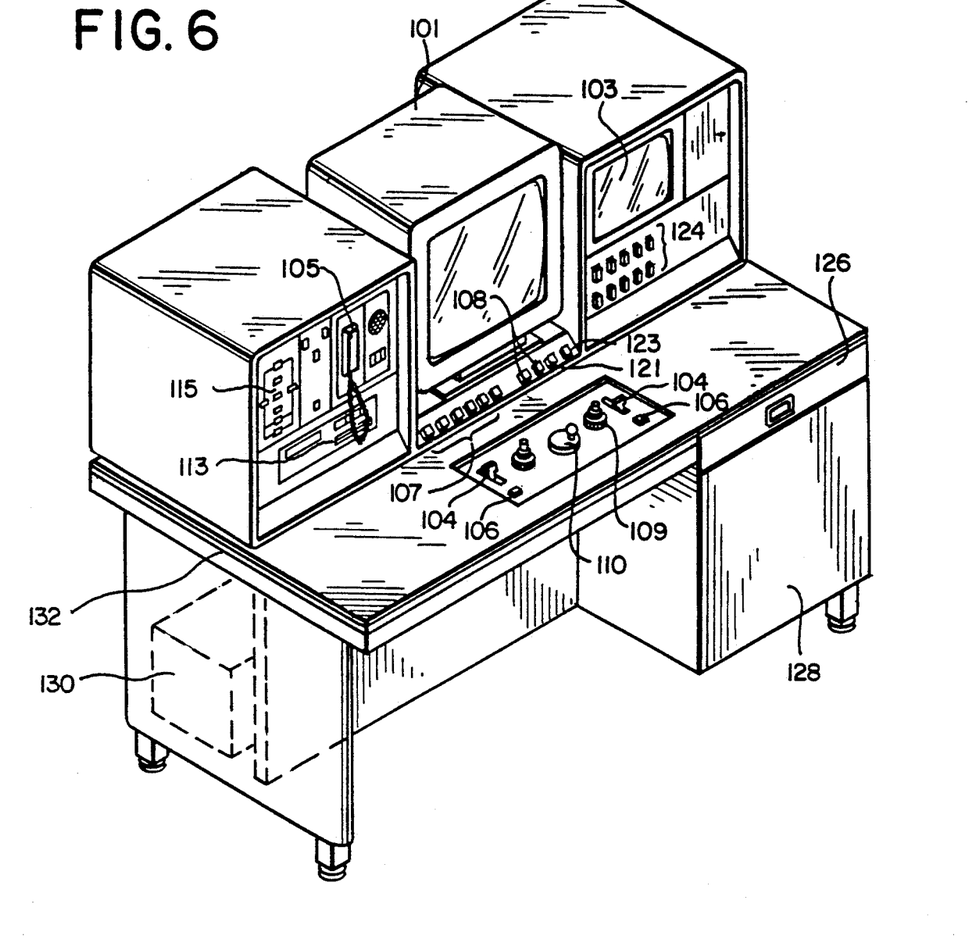
FIG. 6 is a perspective view of a pathologist workstation arranged according to a preferred embodiment of the present invention.

FIG. 6, which is a perspective view of a pathologist workstation, shows the preferred arrangement of its various components. The workstation includes a console 132. In the lower portion of the console 132 is a power back-up system 130, such as a set of batteries.

A microprocessor is included in the other lower portion 128 of the console 132. A keyboard for this microprocessor is preferably stored in the drawer 126. As a preferred example, the microprocessor at the workstation can be an IBM AT which is equipped with 3 megabytes of random access memory, an enhanced graphics card and monitor, 2 serial ports, and 1 parallel port. This computer can be programmed according to the source code listing attached hereto as Appendix B.

Sitting on the console is a specimen viewing monitor 101. As a preferred example, an Ikegami high resolution monitor with catalog No. TM-14 9 RH/N/RGB can be used. This monitor is compatible with the Ikegami 370-m video camera referred to above. The resolution of this particular monitor is 525 lines.

A telephone 105 is preferably provided as part of the workstation to facilitate oral communication between the pathologist and the attending physician or the consulting pathologist, if any. The telephone 105 is preferably equipped with a headset and as a speaker phone so that it can be used by the pathologist without using his hands.

The workstation also includes a control panel 115 with a lighted display to monitor the integrity of the bidirectional communication linkages between the workstation and the microscope at the remote site.

The workstation includes microscope control means which generate control signals to be sent to the microscope. Preferably, a right and left set of the controllers is provided in order to accommodate both right and left-handed pathologists.

In this embodiment, the movement of the stage is controlled by the directional wheel 110, either the right or the left speed slide controls 104, and either the right or the left start/stop buttons 106. In particular, the direction in which the stage is moved is controlled by turning the directional wheel 110 so that its knob points in the desired direction. The speed at which the stage is moved is controlled by either of the slide controls 104, i.e. pushing it away from the pathologist increases the speed of the movement and vice versa. The start/stop buttons 106 start the movement when pushed the first time and stop the movement when pushed the second time. This combination of the start/stop buttons with the slide controls is advantageous in that when the button is pushed to start the movement again, it will proceed at the same speed as before assuming the slide control was not moved.

Alternatively, the movement of the stage is controlled by a joy stick. For example, a CH Products Precision Analog Joystick can be used. Other alternatives for moving the stage include using a "mouse," tracking ball, or simple directional keys.

Figure 7:
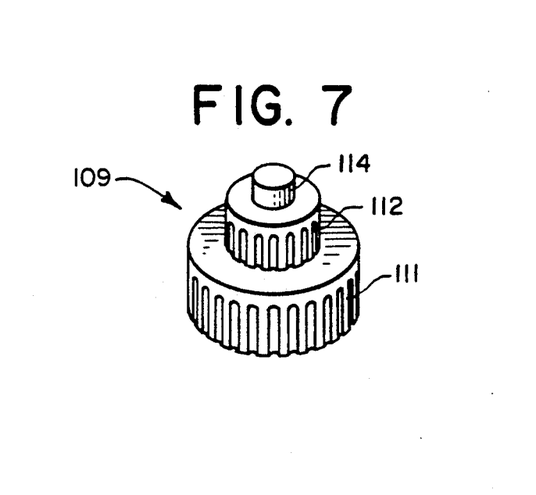
FIG. 7 is a perspective view of a combined focus control and marking button for use at the pathologist workstation depicted in FIG. 6.

The focus of the microscope can be controlled by either the right or left stacked focus controls 109. FIG. 7 is an enlarged view of one of these controls. The larger knob 111 controls the coarse focus for the microscope. The smaller knob 112 controls the fine focus. The multi-function controller 109 also includes a button 114 which can be pressed to select a particular site on the specimen. By means to be discussed below, the coordinates of such points, which points correspond to the center of the microscopic field, will be stored and available to automatically return the specimen to those points. In addition, pressing the button 114 twice in rapid succession will cause the video printer 113 to produce a photographic copy of the image currently viewed on the screen 101.

A series of buttons 107 is provided for selecting the magnification of the microscope. Typically, the microscope will have six objective lenses to produce between 2× and 100× magnification. Accordingly, the series of buttons 107 will typically be six in number.

A pair of buttons 108 is provided for selecting the level of illumination of the specimen. Pressing the left button increases the illumination of the specimen by one step while pressing the right button decreases the illumination by one step.

The button 121 can be pressed to initiate an autoscan mode whereby the entire specimen is scanned according to a predetermined pattern and at the magnification selected by one of the buttons 107.

Figure 8:
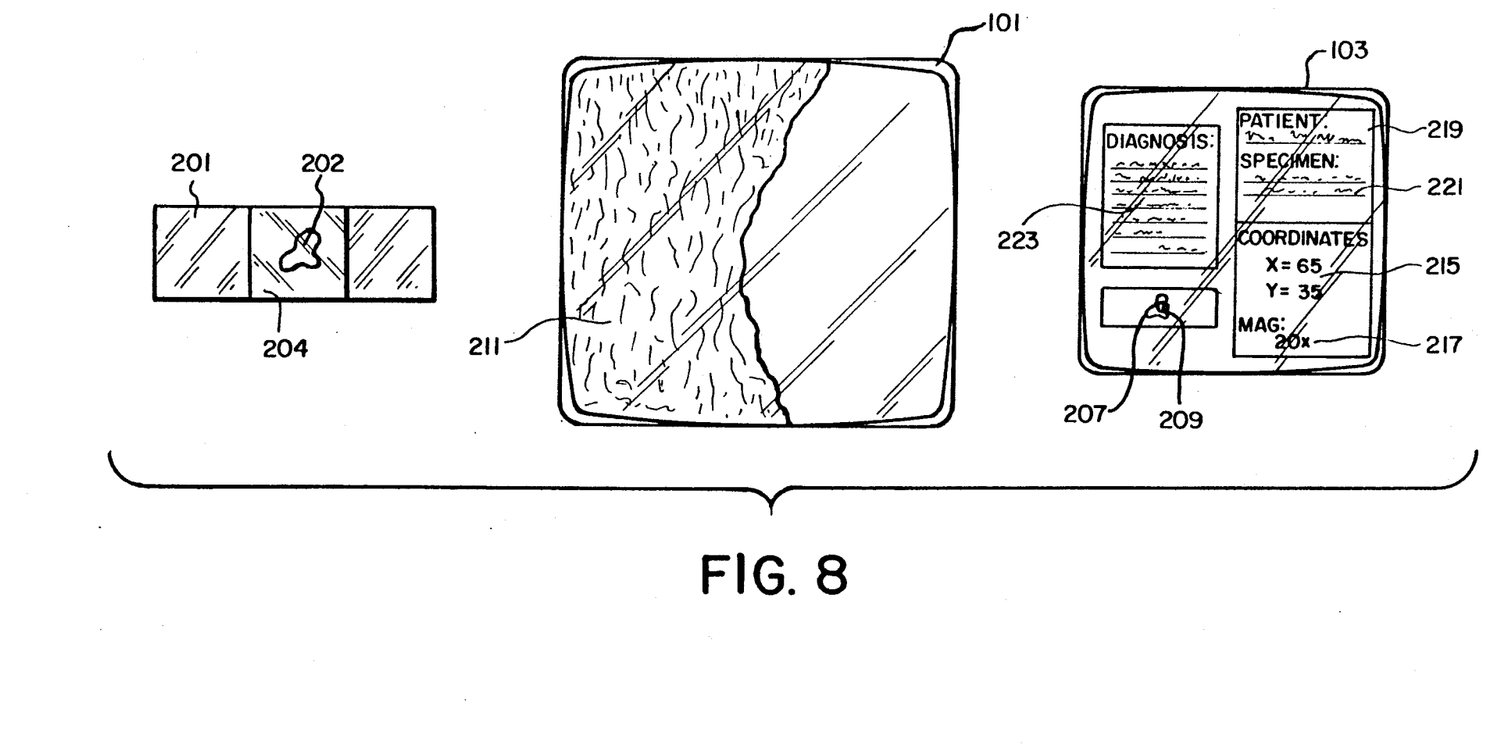
FIG. 8 is a representation of the mapping function of the pathologist workstation according to the most preferred embodiment of the present invention.

In accordance with the most preferred embodiment which is depicted in FIG. 8, the workstation also includes mapping and tracking means for generating and graphically displaying a map 207 of the specimen being viewed, i.e. a representation of the shape of the specimen. This mapping and tracking feature of this embodiment is considered to be highly desirable in the context of the invention. In particular, because the pathologist does not have the slide in his possession, he will have a more difficult time insuring that he has seen the whole specimen.

This map 207 is preferably displayed on the control monitor 103. After the map is generated and displayed, the relative position of the field being viewed is shown on this map, e g. by a colored empty circle 209. Most preferably, the diameter of the circle 209 on the map will represent the actual diameter of the microscopic field 211 currently viewed on the monitor 101, i.e. the size of the circle will be adjusted according to the magnification selected.

The specimen 202 is mounted on glass slide 201 with a cover slip 204. The mapping and tracking means generates the map 207, i.e. the silhouette showing the shape of the specimen, in a window on the control monitor 103. Also appearing on the control monitor is identification information about the patient 219 and about the specimen 221 which has been entered from the remote site and possibly added to at the workstation. Also, space 223 is provided on the control monitor 103 for the pathologist to enter his diagnostic opinion for this particular specimen using the keyboard in drawer 126.

In addition, the control monitor shows other microscope parameters such as the X and Y coordinates 215 of the field currently being viewed. These coordinates are obtained from location signals sent from the microscope, preferably determined using the lower left hand corner of the slide as X=0 and Y=0. Also the control monitor should display the power 217 at which the specimen is currently magnified. Typically, the power will correspond with the particular objective lens selected. The control monitor 103 can also show the level of illumination of the specimen.

Most preferably, the mapping and tracking means comprises a second video camera which is adapted to collect an image of the entire specimen slide. This video image is digitized and converted into a simple silhouette of the specimen, for example by an image grabber board on the microprocessor, and then sent to the workstation. Because most microscopes are not adapted to illuminate the entire specimen at one time, it is currently preferred to provide a second video camera positioned over a light box that can illuminate the entire slide. In such an embodiment it is important that means are provided to secure the slide in the exact spot so that the X and Y coordinates of the map produced will correspond exactly with those sent from the motorized stage of the microscope.

Alternatively, the mapping and tracking means comprises a digital computer programmed to generate control signals which cause the entire specimen to be scanned. The computer is further programmed to interpret the video signals received so as to determine the X and Y coordinates of the periphery of the specimen to thereby generate said map. This map is thereafter displayed on the control monitor as a silhouette such as that shown in FIG. 8. The computer is further programmed to display the location of the field currently being viewed on the map. This is done by converting the location signals received from the microscope into X and Y coordinates.

The digital computer of the preferred mapping and tracking means is also programmed to store pairs of X and Y coordinates for points which are selected by the pathologist during viewing. These pairs of coordinates can be used by the digital computer to automatically return the specimen to these selected points. To facilitate this return, buttons are provided which when pushed will automatically generate the control signals so that the slide will be moved to where the microscope field of interest returns to the monitor 101. A button 123 is provided which will automatically return the slide to the first selected position. Pressing this button again will cause the slide to be returned to the second position, and so forth. In addition, a series of ten buttons 124 is provided. These buttons correspond to the order of the fields that were selected. That is, pressing button number 7 will return the slide so that the seventh field selected by the pathologist will be returned to the monitor 101. Preferably, the buttons 124 are capable of being lit so as to indicate how many points have been selected on that specimen. Certainly, more than ten buttons can be provided if needed. It is also desirable to store with each pair of coordinates the power of magnification at which the point of interest was viewed so that that can automatically be returned as well.

These pairs of coordinates can also be stored as part of the pathologists report to document the microscopic fields of diagnostic interest and for comparative purposes. Such documentation is desirable in the context of this invention because the slides upon which the diagnostic opinions are rendered will be archived at a remote site.

The workstation preferably also includes a video printer 113 which can make a photographic copy of the image which is currently on the viewing monitor 101. As stated above, this can be enabled by pressing the button 114 two times quickly.

As can be seen, there has thus been provided a system for allowing a pathologist located at a diagnostic center to render pathology diagnostic opinions in connection with specimens located at a site which is remote from the diagnostic center. It should be noted that although the invention has been described in terms of preferred embodiments and examples, that these description should not be taken to limit the scope of the invention as defined in the appended claims.

I claim:

1. A telepathology diagnostic system which allows a pathologist located at a diagnostic center to render pathology diagnostic opinions in connection with specimens located at a site which is remote from the diagnostic center, which system comprises:

a microscope located at the remote site including robotic means for adjusting the relative position of a specimen to the lens, the magnification of the specimen, and the focus of the specimen;

video camera means for collecting video signals from the microscope;

bidirectional communication means for communicating signals between the remote site and the diagnostic center;

a pathologist workstation located at the diagnostic center and comprising a monitor for viewing the video signals collected by the video camera means which signals are sent over the bidirectional communication means, and further comprising microscope control means by which the pathologist generates control signals which are sent over the bidirectional communication means to the robotic means of the microscope so that the pathologist can thereby remotely adjust the relative position of the specimen to the lens, the magnification of the specimen, and the focus of the specimen; and means for determining and storing coordinates corresponding to the relative position of the specimen to the lens of selected microscopic fields of interest;

whereby the system provides the pathologist located at the diagnostic center with the ability to remotely adjust the relative position of the specimen to the lens, the magnification of the specimen, and the focus of the specimen to thereby make observations of various microscopic fields on the specimen necessary for rendering a pathology diagnostic opinion, and the ability to store the coordinates of said selected microscopic fields of interest for later reference.

2. The system of claim 1 wherein the coordinates are determined and stored in the form of X, Y and Z coordinates.

3. The system of claim 2 wherein the means for determining and storing the coordinates of selected microscopic fields includes means associated with the microscope for generating location signals in the form of X, Y and Z coordinates of microscopic fields being viewed, which location signals are continuously sent over the bidirectional communication means to the pathologist workstation and means operable by the pathologist for selecting various microscopic fields as microscopic fields of interest for which the X, Y and Z coordinates are stored.

4. The system of claim 3 wherein the means for selecting various microscopic fields as microscopic fields of interest comprise a series of buttons, each corresponding to a selected field.

5. The system of claim 4 wherein the buttons are each numbered.

6. The system of claim 4 wherein each of the buttons are configured so that, when pressed a first time for a given sample, a microscopic field of interest is selected, and so that, when pressed a subsequent time, the specimen is returned to that microscopic field of interest.

7. The system of claim 4 wherein each of the buttons light up a field has been selected with that button.

8. The system of claim 3 further comprising means for generating control signals which cause the specimen to be returned to the microscopic fields of interest previously selected by the pathologist.

9. The system of claim 8 further comprising means for generating magnification return control signals which cause the magnification of the microscope to be returned to that which was being used when said microscopic fields of interest were selected.

10. The system of claim 1 wherein the pathologist workstation further comprises means for electronically storing video images of the microscopic fields of interest.

11. The system of claim 10 further comprising means for reproducing said video images.

12. A telepathology diagnostic system which allows a pathologist located at a diagnostic center to render pathology diagnostic opinions in connection with specimens located at a site which is remote from the diagnostic center, which system comprises:

a microscope located at the remote site including robotic means for adjusting the relative position of a specimen to the lens, the magnification of the specimen, and the focus of the specimen;

video camera means for collecting video signals from the microscope;

bidirectional communication means for communicating signals between the remote site and the diagnostic center;

a pathologist workstation located at the diagnostic center and comprising a monitor for viewing the video signals collected by the video camera means which signals are sent over the bidirectional communication means, and further comprising microscope control means by which the pathologist generates control signals which are sent over the bidirectional communication means to the robotic means of the microscope so that the pathologist can thereby remotely adjust the relative position of the specimen to the lens, the magnification of the specimen, and the focus of the specimen to thereby observe microscopic fields of interest; and means for storing video images of selected microscopic fields of interest;

whereby the system provides the pathologist located at the diagnostic center with the ability to remotely adjust the relative position of the specimen to the lens, the magnification of the specimen, and the focus of the specimen to thereby make observations of various microscopic fields on the specimen necessary for rendering a pathology diagnostic opinion, and the ability to select microscopic fields of interest and have the video image of said selected microscopic fields of interest stored.

13. The system of claim 12 further comprising means for reproducing said video images.

14. The system of claim 13 further comprising means for storing a video image of said selected microscopic fields of interest.

15. The system of claim 12 further comprising means for photographically reproducing said video images.

16. A telepathology diagnostic system which allows a pathologist located at a diagnostic center to render pathology diagnostic opinions in connection with specimens located at a site which is remote from the diagnostic center, which system comprises:
- a microscope located at the remote site including robotic means for adjusting the relative position of a specimen to the lens, the magnification of the specimen, and the focus of the specimen, and means for generating locations signals corresponding to the relative location of the specimen to the lens;
- video camera means for collecting video signals from the microscope;
- bidirectional communication means for communicating signals between the remote site and the diagnostic center;
- a pathologist workstation located at the diagnostic center and comprising a monitor for viewing the video signals collected by the video camera means which signals are sent over the bidirectional communication means, and further comprising microscope control means by which the pathologist generates control signals which are sent over the bidirectional communication means to the robotic means of the microscope so that the pathologist can thereby remotely adjust the relative position of the specimen to the lens, the magnification of the specimen, and the focus of the specimen;
- means for selecting microscopic fields of interest and for converting the location signals into coordinates corresponding to the relative position of the specimen to the lens at said selected microscopic fields of interest; and
- means for storing said coordinates;
- whereby the system provides the pathologist located at the diagnostic center with the ability to remotely adjust the relative position of the specimen to the lens, the magnification of the specimen, and the focus of the specimen to thereby make observations of various microscopic fields on the specimen necessary for rendering a pathology diagnostic opinion, and the ability to store the coordinates of said selected microscopic fields of interest for later reference.

17. The system of claim 16 wherein the coordinates are determined and stored in the form of X, Y and Z coordinates.

18. The system of claim 16 further comprising means for automatically returning to each of said selected microscopic fields of interest.

19. The system of claim 16 further comprising means for reproducing said video images.

20. The system of claim 16 wherein the means for selecting various microscopic fields as microscopic fields of interest comprise a series of buttons, each corresponding to a selected field, and wherein each of the buttons are configured so that, when pressed a first time for a given sample, a microscopic field of interest is selected, and so that, when pressed a subsequent time, the specimen is returned to that microscopic field of interest.

* * * * *